United States Patent
Saxena et al.

(10) Patent No.: US 6,831,101 B2
(45) Date of Patent: Dec. 14, 2004

(54) TRICYCLIC RANTES RECEPTOR LIGANDS

(75) Inventors: Geeta Saxena, Vancouver (CA); Christopher R. Tudan, Vancouver (CA); Ahmed Merzouk, Richmond (CA); Hassan Salari, Delta (CA)

(73) Assignee: Chemokine Therapeutics Corporation, Vancouver (CA)

( * ) Notice: Subject to any disclaimer, the term of this patent is extended or adjusted under 35 U.S.C. 154(b) by 0 days.

(21) Appl. No.: 09/992,550

(22) Filed: Nov. 13, 2001

(65) Prior Publication Data

US 2003/0125380 A1 Jul. 3, 2003

Related U.S. Application Data

(63) Continuation-in-part of application No. 09/881,559, filed on Jun. 14, 2001.

(51) Int. Cl.[7] .................... A61K 31/215; A61K 31/19
(52) U.S. Cl. ...................... 514/529; 514/569
(58) Field of Search ................. 514/529, 569

(56) References Cited

U.S. PATENT DOCUMENTS

| 4,282,253 A | 8/1981 | Steck ............... 424/330 |
| 6,039,966 A | 3/2000 | Kostka et al. |
| 6,365,634 B1 | 4/2002 | Russell et al. ........ 514/736 |

FOREIGN PATENT DOCUMENTS

| DE | 25 19 943 | 12/1975 |
| DE | 25 35 930 | 3/1976 |
| DE | 31 13 460 | 10/1982 |
| EP | 0 774 254 A1 | 5/1997 |
| WO | WO 92/18119 | 10/1992 |
| WO | WO 97/41849 | 11/1997 |
| WO | WO 97/42156 | 11/1997 |
| WO | WO 01/34143 | 5/2001 |

OTHER PUBLICATIONS

English abstract of Giuseppe, DE 3113460.*
Abstract of Moreland et al., Am. J. Med. Sci., 1993; 305(1): 40–51.*
Volkman, John K. et al, (1993) J. Chromatogr. 643 (1–2) 209–219.
Nogueria, J.M.F. et al, (1994) J. Anal. Chem. 350 (6) 379–383.
Hitchison, M. et al, (1984) J. Chem. Soc., Perkin Trans I, 2363.
Claude, C.A. et al, (1975) Journal of Immunology 114 (5) 1537–1540.
Hosseimi, H. et al (2000) Neurology 54 (7) A166, an abstract presented in Apr. 2000 on "Inhibition of proteosome prevents clinical signs in an experimental model of Multiple Sclerosis".

(List continued on next page.)

*Primary Examiner*—San-Ming Hui
(74) *Attorney, Agent, or Firm*—Bret E. Field; Bozicevic, Field & Francis

(57) ABSTRACT

In various aspects, the invention provides compounds that bind to one or more RANTES receptors for the treatment of chemokine mediated disease states, such as compounds of formula (I):

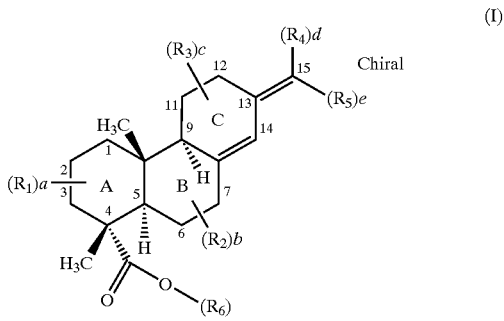

2 Claims, 3 Drawing Sheets

OTHER PUBLICATIONS

Patent Abstracts of Japan vol. 1999, No. 03, Mar. 31, 1999 & JP 10 338632 A (Tanabe Seiyaku Co Ltd), Dec. 22, 1998 abstract.

Patent Abstracts of Japan vol. 1999, No. 11, Dec. 26, 1995 & JP 07 224038 A (Mitsui Toatsu Chem Inc), Aug. 22, 1995 abstract.

Patent Abstracts of Japan vol. 012, No. 462 (C–549), Dec. 5, 1988 & JP 63 183512 A (Shiseido Co Ltd; Others: 01), Jul. 28, 1988 abstract.

Patent Abstracts of Japan vol. 011, No. 262 (C–442), Aug. 25, 1987 & JP 62 063518 A (Arakawa Chem Ind Co Ltd; Others: 01), Mar. 20, 1987 abstract.

Ryu, Shi Yong, et al., "In vitro antitumor activity of diterpenes from *Aralia cordata*", Database accession No. 124:278274 HCA XP–002215368 abstract.

Loder, J.W., et al., "Tumor–inhibitory plants. New alkaloids from the bark of *Erythrophleum chlorostachys* (Leguminosae)", Database accession No. 80:68397 HCA XP–002215369 abstract.

Yarimizu, T., et al., "Protective effects of an antiucler agent, ecabet sodium on colorectal carcinogenesis in rodents", Database accession No. 1998350266 XP–002215370 abstract.

El–Sayed, et al., "Diterpene constituents of *Juniperus polycarpos* and their antimicrobial and anti–inflammatory activities", Database accession No. 132:47500 HCA XP–002215371 abstract.

Kosela, Soleh, et al., "Effects of diterpene acids on malondialdehyde generation during thrombin induced aggregation of rat platelets", Database accession No. 106:131390 HCA XP–002215372 abstract.

Han, Koo Dong, et al., "Chemistry and pharmacology of diterpenoids of *Siegesbeckia pubescens*", Database accession No. 84:150777 HCA XP–002215373 abstract.

Han, Byung Hoon, et al., "Studies on the antiinflammatory activity of *Aralia continentalis*. I. Characterization of continentalic acid and its antiinflammatory activity", Database accession No. 99:136826 HCA XP–002215374 abstract.

Kinouchi, Yoshitaka, et al., "Potential Antitumor–Promoting Diterpenoids from the Stem Bark of *Picea glehni*", *Journal of Natural Products*, vol. 06, No. 6, 2000, pp. 817–820.

Okuyama, E., et al., "Analgesic principles from *Aralia cordata* Thunb", *Chemical & Pharmaceutical Bulletin*, vol. 39, No. 2, Feb. 1991, pp. 405–407.

Shimizu, Mineo, et al., "Anti–inflammatory constituents of topically applied crude drugs. II. Constituents and anti–inflammatory effect of *Cryptomeria japonica* D. Don", *Chem. Pharm. Bull.*, vol. 36, No. 10, 1988, pp. 3967–3973.

* cited by examiner

Figure 1. Inhibition of $^{125}$I-RANTES Binding by CTCM189
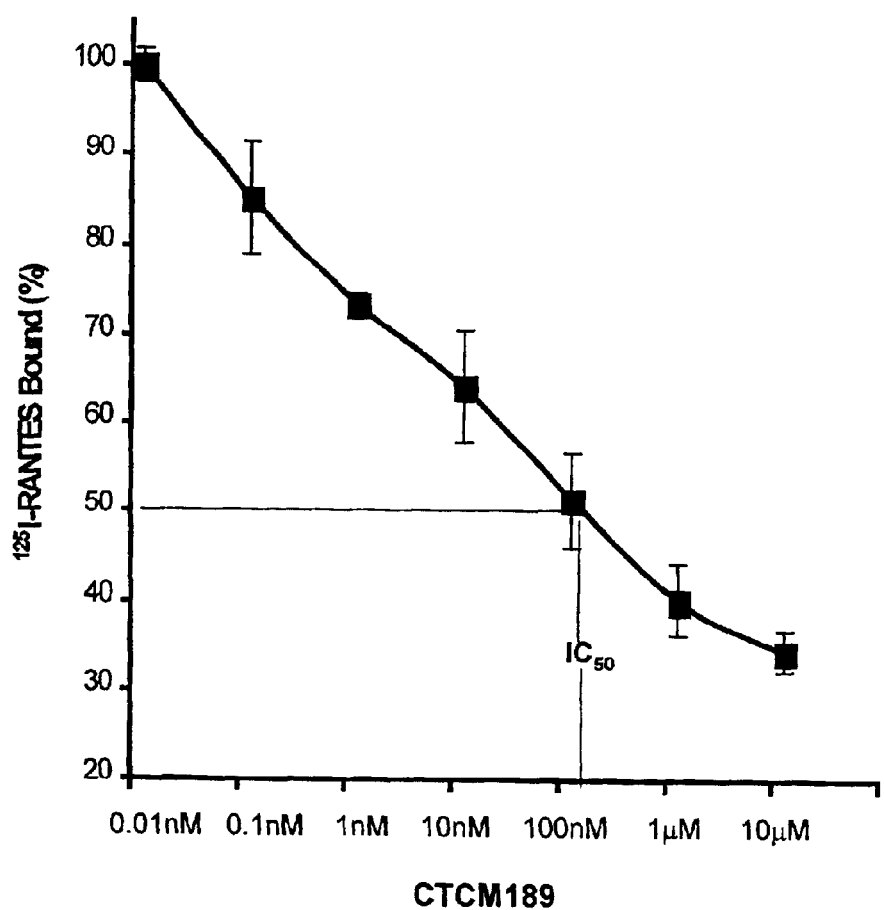

Figure 2. Inhibition of RANTES-induced Calcium Mobilization by CTCM189
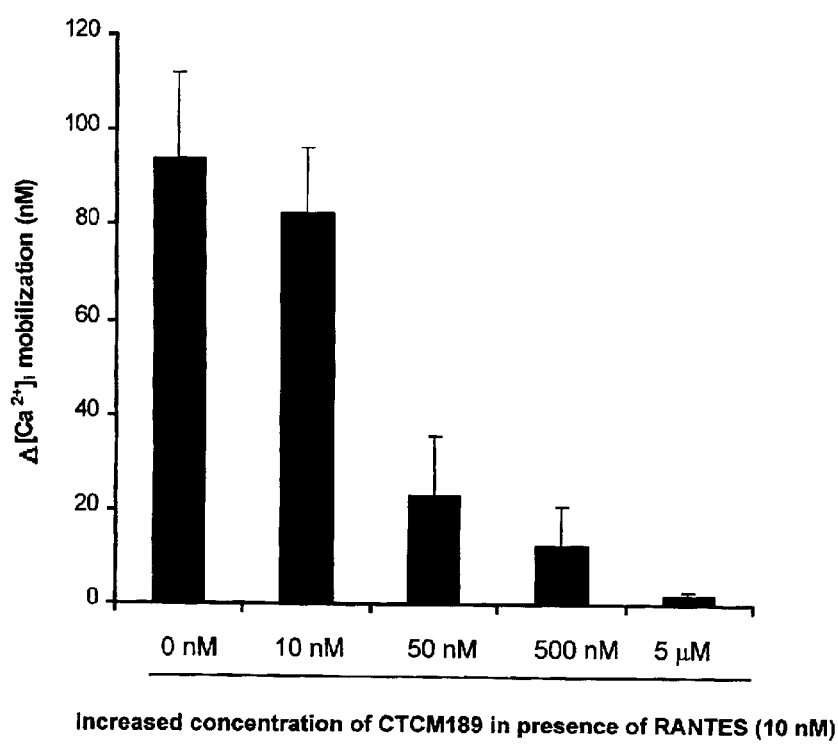

Figure 3. Effect of CTCM189 on EAE Mice Model of Multiple Sclerosis
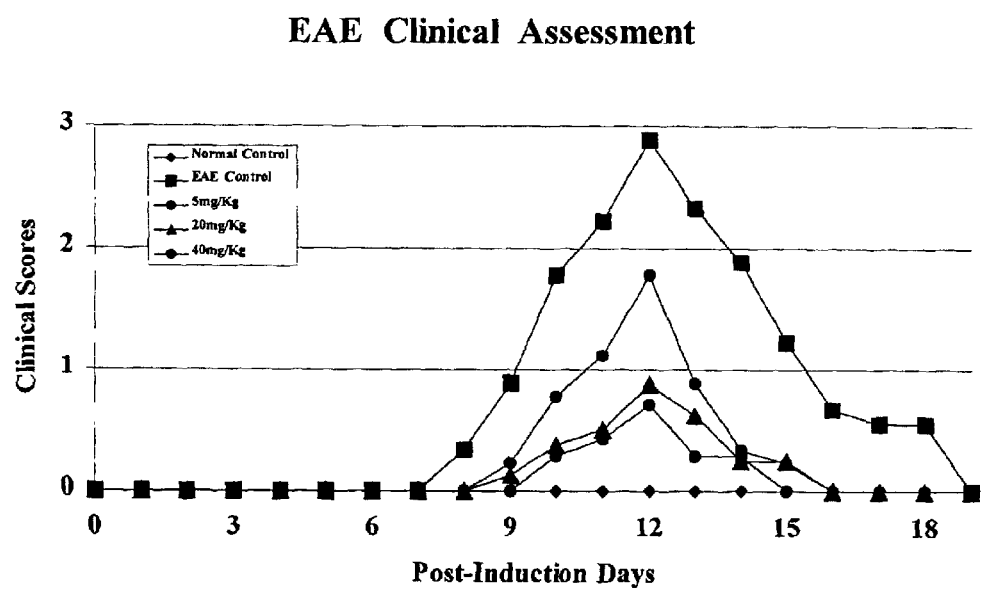

TRICYCLIC RANTES RECEPTOR LIGANDS

This application is a continuation in part of Ser. No. 09/881,559 filed Jun. 14, 2001.

FIELD OF THE INVENTION

The invention is in the field of therapeutic organic compounds.

BACKGROUND OF THE INVENTION

The recruitment of inflammatory cells into sites of inflammation is a normal physiological response designed to fight infection, remove damaged cells, and stimulate healing. However, the excessive recruitment of such cells often exacerbates tissue damage, slows healing, and in some cases leads to host death. Therefore, inhibition of inflammatory cell recruitment may be an appropriate therapeutic strategy in a number of inflammatory diseases, such as asthma, reperfusion injury, arthritis, and inflammatory bowel disease.

Chemokines constitute a diverse group of small secreted basic cytokine proteins that are shown to regulate the chemotactic migration and activation of a number of different leukocytes, particularly in the context of activation of the immune response during inflammatory conditions.

Examples of cells that have been shown to respond to chemokines, and in some cases become activated by chemokines, are neutrophils, eosinophils, basophils, monocytes, macrophages, B lymphocytes and different types of T lymphocytes, and stem cells as well as cancer cells.

Based on structural similarity, chemokines may be subdivided into four subfamilies, CXC, C—C, C and $CX_3C$, depending on the position of their first two cysteine residues. To date, at least 16 chemokine receptors, including nine CC-chemokine receptors and five CXC-chemokine receptors, have been identified and several more might be discovered The chemokine known as RANTES (an abbreviation of the phrase "raised on activation, normal T-cell derived and secreted"), has a sequence of 68 amino acid residues which identifies it as a beta-chemokine, a member of the C—C chemokine subfamily which includes monocyte chemoattractants such as MIP-1 alpha, MIP-1 beta, MCP-1, MCP-2, and MCP-3. Although RANTES was originally identified in activated T lymphocytes, it has also been found to be inducible in a variety of cell types upon stimulation. Initial studies on RANTES-induced chemotaxis indicated that it elicits migratory responses of monocytes and memory T lymphocytes without showing any effect on neutrophiles. RANTES is reportedly a potent attractor for eosinophils, $CD4^+$, $CD45RO^+$ T-cells and basophiles. A receptor for RANTES has been cloned, which has been shown to bind chemokines in the order of affinity of MIP-1 alpha>RANTES. RANTES chemokine receptor CCR-3 was cloned from a human monocyte or an eosinophil library and subsequently shown to bind eotaxin, RANTES, and MCP-3.

A number of studies have suggested a role for RANTES in rheumatoid arthritis. Both RANTES mRNA and protein appear to be up-regulated in rheumatoid arthritis. Antibodies against RANTES significantly decreased the severity of ongoing clinical disease in a rat adjuvant-induced rheumatoid arthritis model.

It has been established that a number of chemokines including, KC, IP-10, MIP-1 alpha, RANTES, MARC (murine MCP-3), and TCA-3 (murine 1–309) are upregulated during the course of murine experimental allergic encephalitis (EAE), a mouse model of multiple sclerosis (MS). It has also been demonstrated that the chemokines JE (murine MCP-1), RANTES, MIP-1 alpha, IP-10, and KC are upregulated in the spinal cord and brain during the acute stages and chronic relapse of murine EAE. Co-localization studies demonstrated that in EAE MIP-1 alpha and RANTES, are produced exclusively by infiltrating leukocytes.

The principle chemokines that are elevated during acute rejection are thought to be those that interact with the receptors CCR-1 and CCR-5 (i.e., MIP-1 alpha, and RANTES) and recruit monocytes and T-cells. This suggests that antagonists that block these receptors might be beneficial for transplant rejection. Enhanced expression of various chemokines in rejected human allograft tissue has been documented, including RANTES. RANTES has also been shown to be elevated in the bronchoalveolar lavage of lung transplant recipients during rejection, especially in patients diagnosed with cytomegalovirus, a complication associated with accelerated rejection. It has also been reported that RANTES expression in cardiac allograft is linked to rejection in an experimental rat model. In humans, RANTES and MIP-1 alpha have been observed in the arteries of heart-transplant recipients undergoing accelerated atherosclerosis.

RANTES has been identified in asthmatic patients after allergen challenge.

Ligands for the CCR-1 receptor (MIP-1 alpha and RANTES) have been implicated in a number of chronic inflammatory diseases, including multiple sclerosis and rheumatoid arthritis. CCR-1 has also been found to play a significant role in allograft rejection. Chemokine receptors, CCR-1 and -5 and their natural ligands, MIP-1 alpha, and RANTES are thought to be involved in glomerular and interstitial lesions of human glomerular disease. CCR-1 is also found to be a major contributor to the airway remodeling responses that arise from *Aspergillus fumigatus*-induced allergic airway disease.

The inflammatory diseases known as acute gouty arthritis and acute pseudogout results from the deposition of monosodium urate monohydrate (MSUM) and Calcium pyrophosphate dihydrate (CPPD) [monoclinic (M) and triclinic (T)] crystals in the synovial joints of human. In the synovial fluid (SF) the crystals become coated with numerous proteins, including opsonizing species such as IgG and complement components. The interaction of protein coated crystals with neutrophils results in neutrophil respiratory burst activity, the generation of reactive oxygen species, degranulation and crystal phagocytosis (McCarty; Pathogenesis and treatment of crystal-induced inflammation.

RANTES, along with the natural ligands for the CCR-5 chemokine receptors, MIP-1 alpha, was found to inhibit human immuno-deficiency virus type-1 (HIV-1) infection, leading to the identification of CCR-5 as the major co-receptor for primary isolates of HIV-1, HIV-2 and SIV-1.

Neoabietic acid [8(14), 13(15)-abietadien-18-oic-acid], is a naturally-occurring tricyclic carboxylic acid of the following formula:

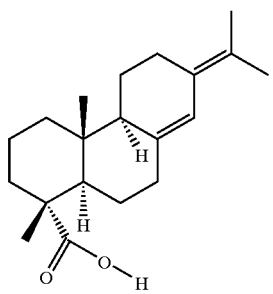

Neoabietic acid (98(14), 13(15)-abietadien-18-oic-acid) is a naturally occurring resin acid found with other diterpene acids in rosin oils. Neoabietic acid is reportedly found in a variety of plants such as: *Picea Schrenkiana, Pinus Palustris, Pinus Sylvastris, Pinus Siberica, Pinus massoniana* and *Pinus Panderosa*. Neoabietic acid may be isolated from natural sources in a variety of ways, such as by solvent-solvent extraction, differential chromatographic techniques, column chromatography, gas chromatography and high-pressure liquid chromatography (Volkman, John K. et. al., (1993) J. Chromatogr. 643 (1–2) 209–219

Neoabietic acid has been suggested to have anti pesticidal uses (Kostka, et al., U.S. Pat. No. 6,039,966 issued Mar. 21, 2000).

SUMMARY OF THE INVENTION

In various aspects, the invention provides compounds that bind to one or more RANTES receptors for the treatment of chemokine mediated disease states. In some embodiments, the invention relates to the methods of using a compound of formula (I), (II), (III), (IV), (V), (VI), (VII), (VIII), (IX), (X), (XI), (XII), (XIII), (XIV) or (XV) or a pharmaceutically acceptable salt thereof, to formulate a medicament for the treatment of a chemokine mediated disease state, or to treat such a disease:

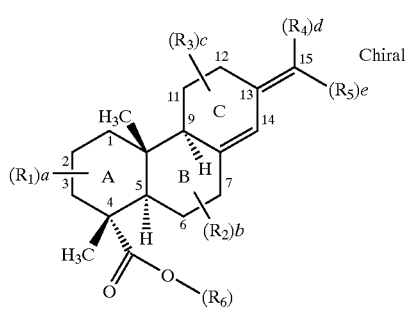

(I)

(II) e.g., Kaurenolide [13013-56-4] (Hitchison, M. et. al., (1984) J. Chem. Soc., Perkin Trans I, 2363)

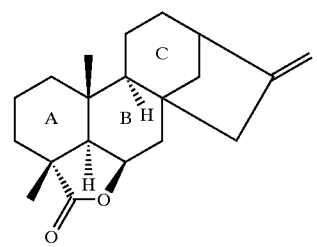

(III) e.g., 7-Oxodehydro-abietic acid; or 7-Oxo-8,11,13-abietatrien-18-oic-acid

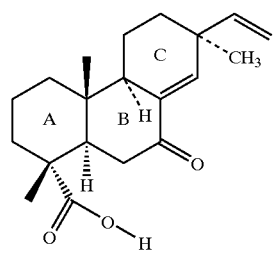

(IV) e.g., alpha-Pimeric acid or [1R-(1 alpha, 4 beta, 4balpha, 7 alpha, 10a beta)]-7-Etheryl-1,2,3,4,4a,5,6,7,9,10,10a-dodecahydro-1,4a,7-trimethyl-1-phenanthrene carboxylic acid, isolated from American Rosin.

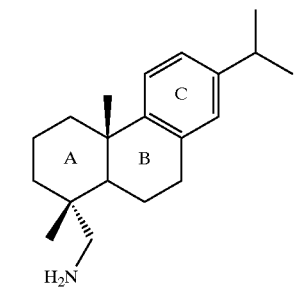

(V) e.g., 1-Phenanthrenemethanamine-1,2,3,4,4a,9,10,10a-octahydro-1,4a-dimethyl-7-(1-methylethyl)-,[1R-(1 alpha, 4a beta,10a alpha)]; or Dehydrabietylamine; or Rosin amine D [1446-61-3] (www.chemfinder.com)

(VI) e.g., 12-Sulfo-dehydroabietic acid; or Ecabet (ref. Merck Index)

5

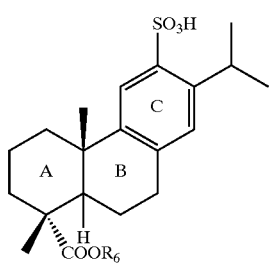

(VII) e.g., Cassamine; or 7-[2-[2-(Dimethylamino)ethoxy]-2-oxoethylidene]tetradecahydro-1,4a,8-trimethyl-9-oxo-1-phenanthrenecarboxylic acid methyl ester; or Erythrophelamine (Merck Index)

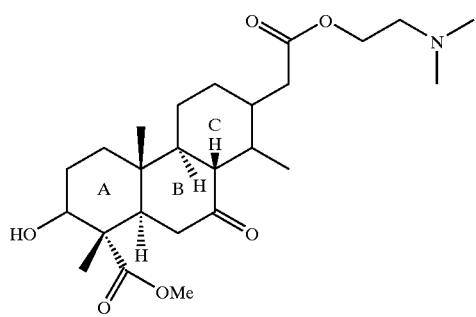

(VIII) e.g., Erythrophleine; or Norcassamidine; or [1S-(1 alpha, 4a alpha, 4b beta, 7E, 8 beta, 8a alpha, 9 alpha, 10a beta)]-Tetradecahydro-9-hydroxy-1,4a,8-trimethyl-7-[2-[2-(methylamino)ethoxy]-2-oxoethylidene]-1-phenanthrenecarboxylic acid methyl ester

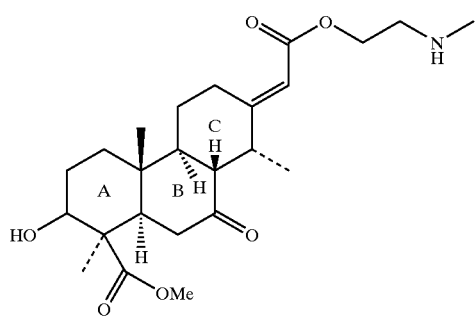

(IX) e.g., Dihydroabietic acid methyl ester [30968-45-7]

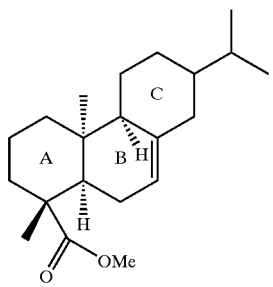

6

(X) e.g., Dehydroabietic acid [1740-19-8]

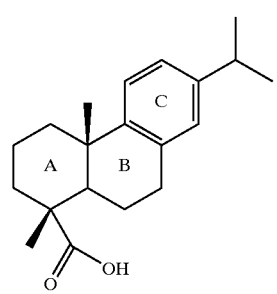

(XI) e.g., Cassaidine; or Dodecahydro-7 beta, 10-dihydroxy-1 alpha,-4b beta, 8,8-tetramethyl-2(1H)-phenanthrenylidene)acetic acid 2-(dimethylamino)ethyl ester (Merck Index)

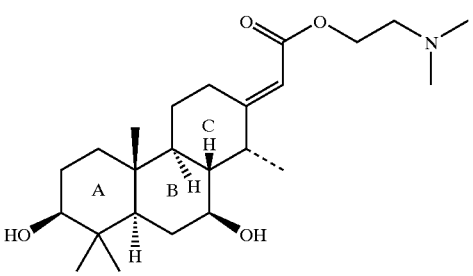

(XII) e.g., Cassaine; or Dodecahydro-7 beta -hydroxy-1 alpha,-4b beta, 8,8-tetramethyl-10-oxo-2(1H)-phenanthrenylidene)acetic acid 2-(dimethylamino)ethyl ester (Merck Index)

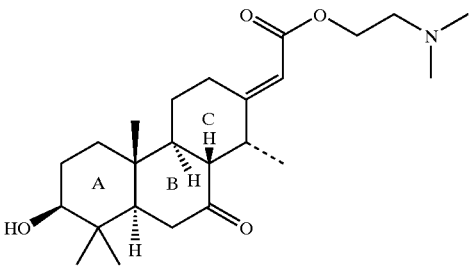

(XIII) e.g., Neoabietic acid [471-77-2]

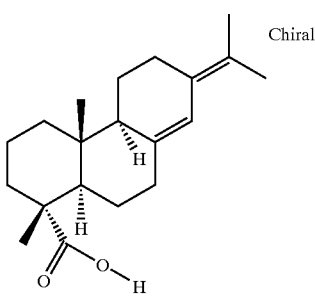

(XIV) Sandaraco-pimaric acid

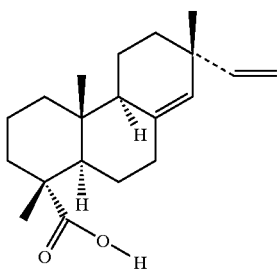

(XV) Ammonium Pimarate

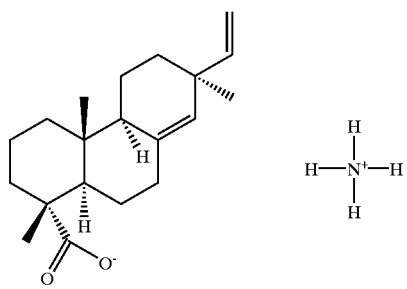

In the foregoing formulae, to the extent that substituents may be added to a given ring structure: "a" may be 0 or an integer from 1 to 8; "b" may be 0 or an integer from 1 to 7; "c" may be 0 or an integer from 1 to 6; "d" may be 0 or an integer from 1 to 10; "e" may be 0 or an integer from 1 to 10.

In alternative embodiments, rings A, B and C may be saturated or unsaturated, non-aromatic or aromatic, and may be substituted with one or more heteroatoms at different positions in the ring, such as oxygen, nitrogen or sulfur heteroatoms.

In alternative embodiments, $R_1$, $R_2$, $R_3$ $R_4$, $R_5$ and $R_6$ at each occurance may independently be selected from substituents having 50 or fewer atoms (such as fewer than 45, 40, 35, 30, 25, 20, 15, 14, 13, 12, 11, 10, 9, 8, 7, 6, 5, 4, 3, or 2) wherein the substituent may be selected from the group consisting of: H; substituted or unsubstitued alkyls, such as: $C_{1-10}$ alkyls, $C_{1-6}$ alkyls; substituted or unsubstituted cycloalkyls, such as $C_{3-6}$ cycloalkyls; substituted or unsubstitued alkenyls, such as $C_{2-6}$ alkenyls; substituted or unsubstitued alkynyls, such as $C_{2-6}$ alkynyls; substituted or unsubstitued aryls; substituted or unsubstitued heterocycles; hydroxyls; aminos; nitros; thiols; primary, secondary or tertiary amines; imines; amides; phosphonates; phosphines; carbonyls; carboxyls; silyls; ethers; thioethers; sulfonyls; sulfonates; selenoethers; ketones; aldehydes; esters; —$CF_3$; —CN; and combinations thereof, wherein the substituents may be linked to a ring, for example $R_4$ and $R_5$ substituents may be linked directly to Ring C (forming an additional ring as in Formula III) and $R_6$ may be linked directly to Ring B. Accordingly, in alternative embodiments, an exocyclic ring structure may be present joining one or more of Rings A, B and C, such as an exocyclic ring involving position $C_3$ and $C_{10}$ or position $C_{18}$ and $C_6$ on Rings A and B. Similarly, an exocyclic ring structure between ring B and ring C may be formed involving $C_8$ and $C_{13}$. These exocyclic rings may be hetrocyclic, may be unsubstituted, or substitutes with one or more hetroatoms, such as nitro, amino, thio, hydro.

In alternative embodiments, compounds of the invention may be used as stereospecific isomers or mixtures thereof, selected on the basis of their chiral centres. There may be one or more chiral centers in the compounds of the invention and such compounds may therefore exist as various stereoisomeric forms. All such stereoisomers are included within the scope of the invention, unless a contrary indication is specifically set out herein. Some compounds may be prepared or isolated as racemates and may be used as such, individual enantiomers may also be isolated or preferentially synthesized by known techniques if desired. Such racemates and individual enantiomers and mixtures thereof are included within the scope of the present invention. Pure enantiomeric forms if produced may be isolated for example by preparative chiral HPLC.

In some embodiments, the chemokine may be RANTES and the chemokine receptor may be selected from the group consisting of CCR-1, CCR-3, CCR-4, and CCR-5.

In various embodiments, the invention provides for the use of compounds of the invention in the treatment of diseases selected from the group consisting of autoimmune diseases, acute inflammation, chronic inflammation, psoriasis, gout, acute pseudogout, acute gouty arthritis, arthritis, rheumatoid arthritis, osteoarthritis, atherosclerosis, cardiovascular, allograft rejection, such as renal allograft, cardiac allograft, kidney transplants, and other chronic transplant rejection, as well as glomerular and interstitial lesions of human glomerular disease, cancer, asthma, mononuclear-phagocyte dependent lung injury, reperfusion injury, idiopathic pulmonary fibrosis, sarcoidosis, focal ischemia, atopic dermatitis, chronic obstructive pulmonary disease, pulmonary fibrosis, adult respiratory distress syndrome, allergic airway disease, acute chest syndrome in sickle cell disease, inflammatory bowel disease, Crohn's disease, ulcerative colitis, septic shock, endotoxic shock, urosepsis, glomerulonephritis, thrombosis, graft vs. host reaction, angiogenesis, atherosclerosis, multiple sclerosis and HIV-1 infections. In various aspects of the invention, alternative RANTES receptor ligands may be used to treat such diseases.

In one aspect, the invention provides methods for the use of neoabietic acid (which may be identified herein as CTCM189), as a chemokine-receptor-binding compound. In alternative embodiments, neoabietic acid may be a chemokine receptor ligand, such as a chemokine receptor agonist or a chemokine receptor antagonist. In some embodiments, neoabietic acid, or pharamaceutically acceptable salts thereof, may be used to treat chemokine or chemokine receptor mediated diseases. In some embodiments, the chemokine may be RANTES and the chemokine receptors may be selected from the group consisting of CCR-1, -3, -4, and -5.

BRIEF DESCRIPTION OF THE DRAWINGS

FIG. 1 shows the inhibitory effect of neoabietic acid (also identified herein as CTCM189) on the binding of RANTES to CCR-1, -3, -4, or -5 receptors using THP-1 cells which express receptors CCR-1, -3, -4, and -5.

FIG. 2 shows Inhibition effect of neoabietic acid (CTCM189) on RANTES-induced $[Ca^{+2}]_i$ mobilization.

FIG. 3 shows neoabietic acid (CTCM189) inhibiting an autoimmune reaction in vivo in the murine Experimental Allergic Encephalomyelitis (EAE) model system.

DETAILED DESCRIPTION OF THE INVENTION

In some embodiments, the compounds of the invention may have a chemokine receptor binding affinity ($IC_{50}$)

below 50 uM, below 10 uM, below 5 uM, below 1 uM, below 100 nM, below 50 nM, below 10 nM or below 1 nM; and may have a selective affinity for a selected chemokine receptor, such as a 10-fold selective affinity, a 50-fold selective affinity or a 100-fold selective affinity, for a selected chemokine receptor relative to an alternative chemokine receptor. For example, in some embodiments, the compounds may have a binding affinity for CCR-1, -3, -4 and -5 of below 50 uM, below 10 uM, below 1000 nM, below 100 nM, below 50 nM, below 10 nM or below 1 nM. Receptor binding affinities may by assayed by any of a number of standard methods, such as competitive displacement of radioactively labeled ligands.

In various aspects, the invention relates to compounds having alternative substitutions and substituent groups, designated in formulae herein as "R", typically with a numeric subscript to identify the substituent group. A substituent group is generally a group that replaces one or more hydrogen atoms attached to a parent structure. The organic substituent groups are for example identified in the Handbook of Chemistry and Physics, 79th Edition, CRC Press (all of which are hereby incorporated by reference). Substituent groups of the invention may for example be selected from groups having from 1 to 100 atoms, such as groups having 100 or fewer, 50 or fewer, 40 or fewer, 30 or fewer, 25 or fewer, 20 or fewer, 15 or fewer, 10 or fewer, 5 or fewer, 4, 3, 2, or 1 atom(s). Atoms in such substituents may for example be selected from the group consisting of carbon, hydrogen, oxygen, nitrogen, halogen, sulfur, silicon, arsenic, boron, selenium and phosphorus.

Substituent groups may for example be substituted or unsubstitued alkyls, such as, $C_{1-10}$ alkyls, $C_{1-6}$ alkyls; substituted or unsubstitued cycloalkyls, such as $C_{1-10}$ cycloalkyls, $C_{3-6}$ cycloalkyls; substituted or unsubstitued alkenyls, such as $C_{1-10}$ alkenyls, $C_{2-6}$ alkenyls; substituted or unsubstitued alkynyls, such as $C_{1-10}$ alkynyls, $C_{2-6}$ alkynyls; substituted or unsubstitued aryls; substituted or unsubstitued heterocycles; hydroxyls; aminos; nitros; thiols; primary, secondary or tertiary amines; imines; amides; amino acids; amino esters; phosphonates; phosphines; carbonyls; carboxyls; silyls; ethers; thioethers; sulfonyls; sulfonates; selenoethers; ketones; aldehydes; esters; —$CF_3$; —CN; thiazoles; pyrazoles; and combinations thereof. Substituent groups which are themselves substituted may be substituted with the similar substituents.

In some embodiments, a substituent group may comprise a cyclic, heterocyclic or polycyclic group. The term "cyclic group", as used herein, includes cyclic saturated or unsaturated (optionally aromatic) group having from 3 to 10, 4 to 8, or 5 to 7 carbon atoms. Exemplary cyclic groups include cyclopropyl, cyclobutyl, cyclopentyl, cyclohexyl, and cyclooctyl. Cyclic groups may be unsubstituted or substituted at one or more ring positions. A cyclic group may for example be substituted with halogens, alkyls, cycloalkyls, alkenyls, alkynyls, aryls, heterocycles, hydroxyls, aminos, nitros, thiols, pyroles; thiazoles, pyrazoles; amines, imines, amides, amino acids, amino esters; phosphonates, phosphines, carbonyls, carboxyls, silyls, ethers, thioethers, sulfonyls, sulfonates, selenoethers, ketones, aldehydes, esters, —$CF_3$, —CN.

The term "heterocyclic group" includes cyclic saturated, unsaturated and aromatic groups having from 3 to 10, 4 to 8, or 5 to 7 carbon atoms, wherein the ring structure includes about one or more heteroatoms. Heterocyclic groups may include pyrane, pyrone, pyrrolidine, oxolane, thiolane, imidazole, oxazole, pyrazole, thiazole, piperidine, piperazine, morpholine. The heterocyclic ring may be substituted at one or more positions with such substituents as, for example, halogens, alkyls, cycloalkyls, alkenyls, alkynyls, aryls, other heterocycles, hydroxyl, amino, nitro, thiol, amines, imines, amides, amino acids, amino esters, phosphonates, phosphines, carbonyls, carboxyls, silyls, ethers, thioethers, sulfonyls, selenoethers, ketones, aldehydes, esters, —$CF_3$, —CN. Heterocycles may also be bridged or fused to other cyclic groups as described below.

The term "polycyclic group" as used herein is intended to refer to two or more saturated, unsaturated or aromatic cyclic rings in which two or more carbons are common to two adjoining rings, so that the rings are "fused rings". Rings that are joined through non-adjacent atoms may be termed "bridged" rings. Each of the rings of the polycyclic group may be substituted with such substituents as described above, as for example, halogens, alkyls, cycloalkyls, alkenyls, alkynyls, hydroxyl, amino, nitro, thiol, amines, imines, amides, esters, phosphonates, phosphines, carbonyls, carboxyls, silyls, ethers, thioethers, sulfonyls, selenoethers, ketones, aldehydes, esters, —$CF_3$, or —CN.

The term "alkyl" refers to the radical of saturated aliphatic groups, including straight chain alkyl groups, branched-chain alkyl groups, cycloalkyl (alicyclic) groups, alkyl substituted cycloalkyl groups, and cycloalkyl substituted alkyl groups. In some embodiments, a straight chain or branched chain alkyl has 20 or fewer carbon atoms in its backbone ($C_1$–$C_{20}$ for straight chain, $C_3$–$C_{20}$ for branched chain), or 10 or fewer carbon atoms. In some embodiments, cycloalkyls may have from 4–10 carbon atoms in their ring structure, such as 5, 6 or 7 carbon rings. Unless the number of carbons is otherwise specified, "lower alkyl" as used herein means an alkyl group, as defined above, having from one to ten carbon atoms in its backbone structure. Likewise, "lower alkenyl" and "lower alkynyl" have chain lengths of ten or less carbons.

The term "alkyl" (or "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, carbonyl (such as carboxyl, ketones (including alkylcarbonyl and arylcarbonyl groups), and esters (including alkyloxycarbonyl and aryloxycarbonyl groups)), thiocarbonyl, acyloxy, alkoxyl, phosphoryl, phosphonate, phosphinate, amino, acylamino, amido, amidine, imino, cyano, nitro, azido, sulfhydryl, alkylthio, sulfate, sulfonate, sulfamoyl, sulfonamido, heterocyclyl, aralkyl, or an aromatic or heteroaromatic moiety. The moieties substituted on the hydrocarbon chain can themselves be substituted, if appropriate. For instance, the substituents of a substituted alkyl may include substituted and unsubstituted forms of aminos, azidos, iminos, amidos, phosphoryls (including phosphonates and phosphinates), sulfonyls (including sulfates, sulfonamidos, sulfamoyls and sulfonates), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The terms "alkenyl" and "alkynyl" refer to unsaturated aliphatic groups analogous in length and possible substitution to the alkyls described above, but that contain at least one double or triple bond respectively.

The term "aralkyl", as used herein, refers to an alkyl or alkylenyl group substituted with at least one aryl group.

Exemplary aralkyls include benzyl (i.e., phenylmethyl), 2-naphthylethyl, 2-(2-pyridyl)propyl, 5-dibenzosuberyl, and the like.

The term "alkylcarbonyl", as used herein, refers to —C(O)-alkyl. Similarly, the term "arylcarbonyl" refers to —C(O)-aryl. The term "alkyloxycarbonyl", as used herein, refers to the group —C(O)—O-alkyl, and the term "aryloxycarbonyl" refers to —C(O)—O-aryl. The term "acyloxy" refers to —O—C(O)—$R_7$, in which $R_7$ is alkyl, alkenyl, alkynyl, aryl, aralkyl or heterocyclyl.

The term "amino", as used herein, refers to —N(R)(R), in which R and R are each independently hydrogen, alkyl, alkyenyl, alkynyl, aralkyl, aryl, or in which R and R together with the nitrogen atom to which they are attached form a ring having 4–8 atoms. Thus, the term "amino", as used herein, includes unsubstituted, monosubstituted (e.g., monoalkylamino or monoarylamino), and disubstituted (e.g., dialkylamino or alkylarylamino) amino groups. The term "amido" refers to —C(O)—N($R_8$)($R_9$), in which $R_8$ and $R_9$ are as defined above. The term "acylamino" refers to —N($R'_8$)C(O)—$R_7$, in which $R_7$ is as defined above and $R'_8$ is alkyl.

The term "amino acids", as used herein, refers to —CH($N^+H_3$)COO—, in which a substitution could be at either or both 'C' and 'N' positions.

The term "amino acid esters", as used herein, refers to —CH(NHCOO$R_{10}$)COO—; where $R_{10}$ is defined as above.

As used herein, the term "nitro" means —$NO_2$; the term "halogen" designates —F, —Cl, —Br or —I; the term "sulfhydryl" means —SH; and the term "hydroxyl" means —OH.

The term "aryl" as used herein includes 5-, 6- and 7-membered aromatic groups that may include from zero to four heteroatoms in the ring, for example, phenyl, pyrrolyl, furyl, thiophenyl, imidazolyl, oxazole, thiazolyl, triazolyl, pyrazolyl, pyridyl, pyrazinyl, pyridazinyl and pyrimidinyl, and the like. Those aryl groups having heteroatoms in the ring structure may also be referred to as "aryl heterocycles" or "heteroaromatics". The aromatic ring can be substituted at one or more ring positions with such substituents as described above, as for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, a heterocyclyl, an aromatic or heteroaromatic moiety, —$CF_3$, —CN, or the like. Aryl groups can also be part of a polycyclic group. For example, aryl groups include fused aromatic moieties such as naphthyl, anthracenyl, quinolyl, indolyl, and the like.

In one aspect, the present invention relates to uses of neoabietic acid (a diterpene acid group compound with chiral functionality):

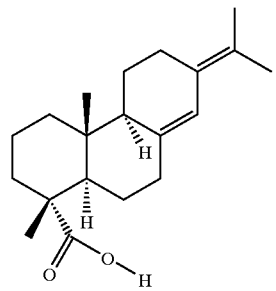

Neoabietic Acid, a Diterpene Acid Group or Phenanthrene Carboxylic Acid Derivative Compound 1

[8(14), 13(15)-abietadien-18-oic-acid] (CAS #471-77-2)

Molecular Formula: $C_{20}H_{30}O_2$

Molecular Weight: 302.46

EXAMPLES

The following examples are illustrative of various aspects of the invention, but are not comprehensive nor limiting with respect to the full scope of the invention.

Receptor Binding

This example discloses the ability of compounds of the invention, such as neoabietic acid (CTCM189), to competitively inhibit binding of the chemokine ligand RANTES to its receptors (CCR-1, -3, -4, and -5) on THP-1 type cells (which express CCR-1, -3, -4, and -5). The binding studies were conducted using $I^{125}$ labeled RANTES as competitor and THP-1 cell lines. FIG. 1 shows the inhibitory effect of neoabietic acid on the binding of RANTES to THP-1 cells expressing CCR-1, -3, -4, and -5. The $IC_{50}$ for the data in FIG. 1 was evaluated at 253 nM. Table 1 shows the results of competitive binding assays, indicating that compounds of the invention are effective to inhibit the binding of RANTES to its receptors.

TABLE 1

Effectivness of Compounds inhibiting $^{125}$I-RANTES Binding

| Compounds | % Inhibition (4 ug/ml) |
| --- | --- |
| A (Neoabietic acid) | 68 |
| B (Sandaraco-pimaric acid) | 36 |
| C (Ammonium Pimarate) | 48 |

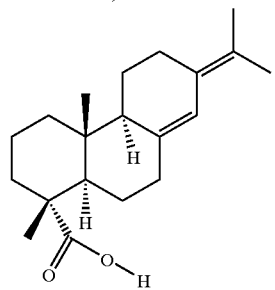

Neoabietic acid
[A]

TABLE 1-continued

Effectivness of Compounds inhibiting $^{125}$I-RANTES Binding

| Compounds | % Inhibition (4 ug/ml) |
|---|---|
| 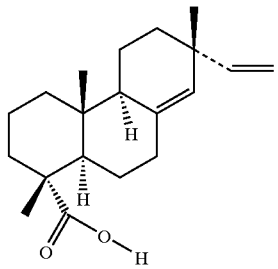 Sandaraco-pimaric acid [B] | 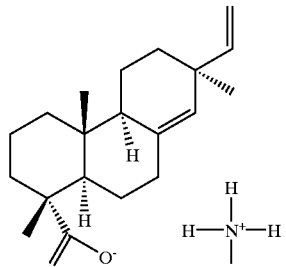 Ammonium Pimarate [C] |

Calcium Release

A rapid, transient rise in the free cytosolic $Ca^{2+}$ concentration ($[Ca^{2+}]_i$) is one of the events in neutrophil activation and is assumed to be involved in many of the subsequent cellular reactions. Both $Ca^{2+}$ release from intracellular stores and $Ca^{2+}$ influx from the extracellular space contribute to the rise in $[Ca^{2+}]_i$. FIG. 2 shows the inhibition of RANTES-induced $[Ca^{2+}]$ mobilization by neoabietic acid (CTCM189) in THP-1 cells. Fura-2,AM loaded THP-1 cells were incubated with CTCM189 for 60 min prior to induction of $[Ca^{2+}]_i$ mobilization by 10 nM RANTES. Result indicate the physiological effect of neoabietic acid (Compound 1) on RANTES-induced $Ca^{2+}$ concentration. The $IC_{50}$ was evaluated at 27.2 nM.

Compound 1 showed an almost complete inhibition of RANTES-induced $[Ca^{2+}]_i$ mobilization in THP-1 cells at the concentration of 5 uM. In accordance with this aspect of the invention, the neoabietic acid, such as compound 1 or corresponding salts may be used for the treatment of a wide range of inflammatory diseases such as gout, arthritis osteoarthritis, rheumatoid arthritis, reperfusion injuries, inflammatory bowl diseases and ARDS.

In Vivo Studies Using the EAE Mouse Model of Multiple Sclerosis

Experimental autoimmune encephalomyelitis (EAE) is a $CD4^+$ Th1-mediated inflammatory demyelinating disease of the central nervous system (CNS) that serves as a model for multiple sclerosis and other autoimmune diseases. It has previously been disclosed that RANTES regulates acute and relapsing autoimmune encephalomyelitis, and that RANTES production in the central nervous system is correlated with relapsing EAE development. In this example, the EAE mouse model (SJL/J mice) for MS is used, in which the disease is induced with *Bordetella pertussis* toxin (Claude C. A. et. al., (1975) *Journal of Immunology* 114(5): 1537–1540 and Hosseimi, H. et. al., (2000) *Neurology* 54 (7): A 166, An abstract presented in April 2000 on "Inhibition of proteosome prevents clinical signs in an experimental model of Multiple Sclerosis"). FIG. 3 demonstrates the activity of neoabietic acid (CTCM189) as an inhibitor of the autoimmune reaction in murine EAE.

Data for FIG. 3 was collected in an experiment involving five groups of 10 mice each, as follows: group I, normal control (no drug, no disease); group II, EAE control (MBP but no drug); group III, drug at 5 mg/kg body weight; group IV, drug at 20 mg/kg body weight; group V, drug at 40 mg/kg body weight. Three different concentrations of neoabietic acid were given to animals for 19 days: 5, 20, and 40 mg/kg/day in a volume of 100 ul Cremophore EL (Sigma). Individual animals were observed daily and graded according to the clinical severity of their disease as follows: grade 0, no abnormality; grade 1, decreased tail tone or slightly clumsy gait; grade 2, tail atony and/or moderately clumsy gait and poor righting ability; grade 3, limb weakness (paraparesis, i.e., partial paralysis of the lower extremities); grade 4, limb paralysis (paraplegia, i.e., paralysis of the lower part of the body including legs); grade 5, severe paralysis/morbidity (quadriplegia or severe paraplegia leading to death). FIG. 3 shows the results, which indicate that tricyclic compounds of the invention such as neoabietic acid have a beneficial effect on the clinical scores of the subject animals compared to a control saline injection.

Therapeutic Formulations

In one aspect, the invention provides a variety of therapeutic uses for phenanthrene carboxylic acid derivative, such as neoabietic acid (1). In various embodiments, the compounds of the invention may be used therapeutically in formulations or medicaments for the treatment of CCR-1, -3, -4 and -5 mediated diseases. The invention provides corresponding methods of medical treatment, in which a therapeutic dose of a compound of the invention is administered in a pharmacologically acceptable formulation. Accordingly, the invention also provides therapeutic compositions comprising compounds of the invention and a pharmacologically acceptable excipient or carrier. The therapeutic composition may be soluble in an aqueous solution at a physiologically acceptable pH.

The invention provides pharmaceutical compositions (medicaments) containing (comprising) compound of the invention. In one embodiment, such compositions include compound of the invention in an effective amount, meaning a therapeutically or prophylactically effective amount, sufficient to modulate CCR-1, -3, -4 and -5 activity, and a pharmaceutically acceptable carrier. In other embodiments, the compositions of the invention may include compound of the invention in a therapeutically or prophylactically effective amount sufficient to modulate the activity of RANTES, and a pharmaceutically acceptable carrier. Compound of the invention may also be used in combination with other compositions and procedures for the treatment of diseases.

A "therapeutically effective amount" refers to an amount effective, at dosages and for periods of time necessary, to achieve the desired therapeutic result, such as modulation of CCR-1, -3, -4, and -5 or RANTES activity. A therapeutically effective amount of a compound of the invention may vary according to factors such as the disease state, age, sex, and weight of the individual, and the ability of compounds of the invention to elicit a desired response in the individual. Dosage regimens may be adjusted to provide the optimum therapeutic response. A therapeutically effective amount is also one in which any toxic or detrimental effects of compounds of the invention are outweighed by the therapeutically beneficial effects.

A "prophylactically effective amount" refers to an amount effective, at dosages and for periods of time necessary, to achieve the desired prophylactic result, such as modulation of CCR-1, -3, -4, and -5 or RANTES activity. A prophylactically effective amount can be determined as described above for the therapeutically effective amount. Typically, since a prophylactic dose is used in subjects prior to or at an earlier stage of disease, the prophylactically effective amount will be less than the therapeutically effective amount.

In particular embodiments, a preferred range for therapeutically or prophylactically effective amounts of compounds of the invention may be 0.1 nM–0.1 M, 0.1 nM–0.05M, 0.05 nM–15 µM or 0.01 nM–10 µM. Alternatively, total daily dose may range from about 0.001 to about 1 mg/kg of patients body mass. Dosage values may vary with the severity of the condition to be alleviated. It is to be further understood that for any particular subject, specific dosage regimens should be adjusted over time according to the individual need and the professional judgement of the person administering or supervising the administration of the compositions, and that dosage ranges set forth herein are exemplary only and are not intended to limit the scope or practice of the methods of the invention.

The amount of a compound of the invention in a therapeutic composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

As used herein "pharmaceutically acceptable carrier" or "excipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, compounds of the invention can be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

The free base of compounds of the invention may be converted if desired, to the monohydrochloride salt by known methodologies, or alternatively, if desired, to other acid addition salts by reaction with other inorganic or organic acids. Acid addition salts may also be prepared metathetically by reacting one acid addition salt with an acid that is stronger than that of the anion of the initial salt. In alternative embodiments, the present invention encompasses the pharmaceutically acceptable salts, esters, amides, complexes, chelates, solvates, crystalline or amorphous forms, metabolites, metabolic precursors or prodrugs of the compounds of the invention.

Sterile injectable solutions can be prepared by incorporating compounds of the invention in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. In accordance with an alternative aspect of the invention, compounds of the invention may be formulated with one or more additional compounds that enhance the solubility of compounds of the invention.

Pharmaceutically acceptable salts include salts that are well known to those skilled in the art such as basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, alicylic acid, phenylacetic acid and mandelic acid. In alternative embodiments, pharmaceutically acceptable cation salts may include alkaline, alkaline earth, ammonium and quaternary ammonium cations.

In accordance with another aspect of the invention, therapeutic compositions of the present invention, comprising compound of the invention, may be provided in containers having labels that provide instructions for use of compounds of the invention to treat chemokine or chemokine receptor mediated diseases, autoimmune diseases, inflammation, acute inflammation, chronic inflammation, psoriasis, gout, acute pseudogout, acute gouty arthritis, arthritis, rheumatoid arthritis, osteoarthritis, atherosclerosis, cardiovascular disease, allograft rejection, chronic transplant rejection, glomerular and interstitial lesions of human glomerular disease, cancer, asthma, mononuclear-phagocyte dependent lung injury, reperfusion injury, idiopathic pulmonary fibrosis, sarcoidosis, focal ischemia, atopic dermatitis, chronic obstructive pulmonary disease, pulmonary fibrosis, adult respiratory distress syndrome, allergic airway disease, acute chest syndrome in sickle cell disease, inflammatory bowel disease. Crohn's disease, ulcerative colitis, septic shock, endotoxic shock, urosepsis, glomerulonephritis, thrombosis, graft vs. host reaction, angiogenesis, atherosclerosis, multiple sclerosis and HIV-1 infections.

Conclusion

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the specification, the word "comprising" is used as an open-ended term, substantially equivalent to the phrase "including, but not limited to", and the word "comprises" has a corresponding meaning. Citation of references herein shall not be construed as an admission that such references are prior art to the present invention. All publications, including but not limited to patents and patent applications, cited in this specification are incorporated herein by reference as if each individual publication were specifically and individually indicated to be incorporated by reference herein and as though fully set forth herein. The invention includes all embodiments and variations substantially as hereinbefore described and with reference to the examples and drawings.

What is claimed is:

1. A method of treating multiple sclerosis in a mammal in need of such treatment, which comprises administering to the mammal an effective amount of a compound of formula (I) or a pharmaceutically acceptable salt thereof:

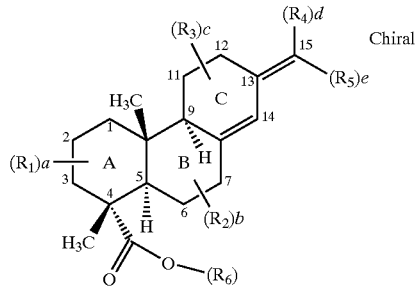

(I)

wherein:

"a" is 0 or an integer from 1 to 8;
"b" is 0 or an integer from 1 to 7;
"c" is 0 or an integer from 1 to 6;
"d" is 0 or an integer from 1 to 10;
"e" is 0 or an integer from 1 to 10;

$R_1$, $R_2$ and $R_3$ at each occurance may independently be selected from substituents having 25 or fewer atoms, wherein the substituent may be selected from the group consisting of: H; substituted or unsubstituted alkyls; substituted or unsubstituted cycloalkyls; substituted or unsubstitued alkenyls; substituted or unsubstitued alkynyls; substituted or unsubstituted aryls;

substituted or unsubstituted heterocycles; hydroxyls; aminos; nitros; thiols; primary, secondary or tertiary amines; imines; amides; phosphonates; phosphines; carbonyls; carboxyls; silyls; ethers; thioethers; sulfonyls; sulfonates; selenoethers; ketones; aldehydes; esters; —$CF_3$; —CN;

$R_4$, $R_5$ and $R_6$ at each occurance may independently be selected from substituents having 20 or fewer atoms, wherein the substituent may be selected from the group consisting of: H; substituted or unsubstitued alkyls; substituted or unsubstitued cycloalkyls; substituted or unsubstitued alkenyls; substituted or unsubstitued alkynyls; substituted or unsubstitued aryls; substituted or unsubstitued heterocycles; hydroxyls: aminos; nitros; thiols; primary, secondary or tertiary amines; imines; amides; phosphonates; phosphines; carbonyls; carboxyls; silyls; ethers; thioethers; sulfonyls: sulfonates; selenoethers: ketones; aldehydes; esters; —$CF_3$,; —$CN$;

$R_1$, $R_2$, $R_3$, $R_4$, $R_5$ and $R_6$ may together define one or more exocyclic rings joining one or more of Rings A, B and C, and an exocyclic ring may be hetrocyclic;

"chiral" denotes that a compound may be chiral.

2. The method of claim 1, wherein the compound has the following formula:

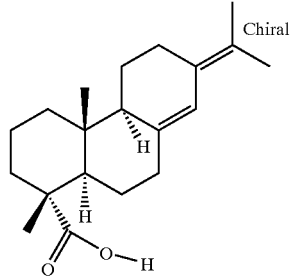

* * * * *